United States Patent
Hernandez et al.

(10) Patent No.: US 11,123,561 B2
(45) Date of Patent: Sep. 21, 2021

(54) SYSTEM COMPRISING A PROBE FOR DETECTING A MASS DISCHARGE OF ACTION POTENTIALS AND A PROBE FOR STIMULATING A VAGUS NERVE OF AN EPILEPSY PATIENT

(71) Applicants: UNIVERSITE DE RENNES 1, Rennes (FR); INSERM (INSTITUT NATIONAL DE LA SANTE ET DE LA RECHERCHE MEDICALE), Paris (FR); CNRS (CENTRE NATIONAL DE LA RECHERCHE SCIENTIFIQUE), Paris (FR); CHU DE RENNES (CENTRE HOSPITALIER UNIVERSITAIRE DE RENNES), Rennes (FR)

(72) Inventors: Alfredo Hernandez, Cesson-sevigne (FR); Benoit Martin, Meung-sur-loire (FR); Arnaud Biraben, Rennes (FR)

(73) Assignees: UNIVERSITE DE RENNES 1, Rennes (FR); INSERM (INSTITUT NATIONAL DE LA SANTE ET DE LA REC, Paris (FR); CNRS (CENTRE NATIONAL DE LA RECHERCHE SCIENTIFIQUE, Paris (FR); CHU DE RENNES (CENTRE HOSPITALIER UNIVERSITAIRE DE, Rennes (FR)

( * ) Notice: Subject to any disclaimer, the term of this patent is extended or adjusted under 35 U.S.C. 154(b) by 0 days.

(21) Appl. No.: 16/076,410

(22) PCT Filed: Feb. 13, 2017

(86) PCT No.: PCT/EP2017/053156
§ 371 (c)(1),
(2) Date: Aug. 8, 2018

(87) PCT Pub. No.: WO2017/137627
PCT Pub. Date: Aug. 17, 2017

(65) Prior Publication Data
US 2019/0091476 A1 Mar. 28, 2019

(30) Foreign Application Priority Data

Feb. 12, 2016 (FR) ...................................... 16/70039

(51) Int. Cl.
*A61N 1/36* (2006.01)
*A61B 5/00* (2006.01)
*A61B 5/24* (2021.01)
*A61B 5/04* (2006.01)

(52) U.S. Cl.
CPC ............ *A61N 1/36053* (2013.01); *A61B 5/24* (2021.01); *A61B 5/4094* (2013.01); *A61N 1/36064* (2013.01); *A61B 5/4836* (2013.01)

(58) Field of Classification Search
CPC ............ A61B 5/004001; A61B 5/4094; A61B 5/4836; A61N 1/36053; A61N 1/36064
See application file for complete search history.

(56) References Cited

U.S. PATENT DOCUMENTS 6,658,287 B1 12/2003 Litt et al.
2006/0052831 A1 3/2006 Fukui
(Continued)

FOREIGN PATENT DOCUMENTS

| JP | 2004283463 A | 10/2004 |
| JP | 2009529352 A | 7/2007 |
| JP | 2009505689 A | 2/2009 |

OTHER PUBLICATIONS

Harreby, K., Sevcencu, C. and Struijk, J., 2010. Early seizure detection in rats based on vagus nerve activity. Medical & Biological Engineering & Computing, 49(2), pp. 143-151 herein Struijk et al. (Year: 2011).*

(Continued)

*Primary Examiner* — Paula J Stice
(74) *Attorney, Agent, or Firm* — Leason Ellis LLP

(57) ABSTRACT

A treatment system for stimulating the vagus nerves is described, comprising the following elements: —a detection (Continued)

and control unit (20); —at least one detection probe (10*d*, 10*g*) connected to the detection and control unit and intended to be applied to at least one of the two vagus nerves of a patient; —means (24) provided in the detection and control unit for detecting a phenomenon of mass discharge of action potentials in at least one vagus nerve using the detection probe or detection probes; —stimulation probes (10*d*, 10*g*) for stimulating vagus nerves, and—means (24) provided in the detection and control unit that are capable, in response to the detection of a mass discharge, of applying predefined asymmetric stimulation signals to said stimulation probes capable of causing a depolarization and/or hyperpolarization of the vagus nerves and of blocking the conduction of the action potentials at least in the efferent direction. The system is intended for preventing the risk of sudden death in the event of an epileptic seizure in epilepsy patients.

23 Claims, 3 Drawing Sheets

(56) References Cited

U.S. PATENT DOCUMENTS

| 2007/0027486 | A1* | 2/2007 | Armstrong | A61N 1/36071 |
| | | | | 607/2 |
| 2007/0255320 | A1 | 11/2007 | Inman et al. | |
| 2014/0275838 | A1* | 9/2014 | Osorio | A61B 5/4094 |
| | | | | 600/301 |
| 2014/0316497 | A1 | 10/2014 | Gaunt et al. | |
| 2020/0324115 | A1* | 10/2020 | Osorio | A61N 1/36185 |

OTHER PUBLICATIONS

International Search Report in corresponding International Patent Application No. PCT/EP2017/053156, dated Mar. 31, 2017. 3 pages.

Japanese Office Action in Corresponding Japanese Patent Application No. 2018-542711 dated Oct. 22, 2020. 8 pages.

* cited by examiner

SYSTEM COMPRISING A PROBE FOR DETECTING A MASS DISCHARGE OF ACTION POTENTIALS AND A PROBE FOR STIMULATING A VAGUS NERVE OF AN EPILEPSY PATIENT

CROSS-REFERENCE TO RELATED PATENT APPLICATIONS

This application is a U.S. National Stage Application under 35 U.S.C. § 371 of International Patent Application No. PCT/EP2017/053156, filed Feb. 13, 2017, which claims the benefit of priority under 35 U.S.C. Section 119(e) of French Patent Application number 16/70039 filed Feb. 12, 2016, which are incorporated by reference in their entireties. The International Application was published on Aug. 17, 2017, as International Publication No. WO 2017/137627 A1.

FIELD OF THE INVENTION

The present invention relates to the field of medical devices intended to prevent the most serious consequences of an epileptic seizure in humans.

More particularly, it relates to a medical device aimed, on the basis of the activity of at least one vagus nerve and preferably both vagus nerves, at identifying the occurrence of an abnormal activity that could be fatal, secondary to an epileptic seizure (the SUDEP phenomenon, which stands for "Sudden Unexpected Death in Epilepsy"), and at reducing this risk by acting on the vagus nerve(s) to eradicate this phenomenon.

STATE OF THE ART

Today, we do not know how to prevent the risk of sudden death, or to eradicate the phenomenon of epilepsy likely to cause sudden death when it occurs.

The closest state of the art is represented by the following documents:

a) document US2014/0142653A1 describes a method for treating a patient suffering from epilepsy, based on the measurement of a physiological signal (typically an electroneurogram, possibly in combination with measurement of the heart rate) making it possible to determine whether the patient is undergoing a seizure, or has just undergone a seizure. Depending on the measurement obtained, the method applies a stimulation on one of the two vagus nerves, or on both, on one side in the efferent direction in order to act on the heart rate, and on the other side in the afferent direction in an attempt to reduce the epileptic phenomenon. This document gives no indication, however, on the way in which an actual risk of sudden death caused by epilepsy can be determined, or on the way in which a stimulation could reduce or even cancel out the risk, or even on the capacity of the method to reduce mortality other than by reducing the epileptic seizures. Thus, it relates only to the treatment of epileptic seizures in general.

b) Document U.S. Pat. No. 8,634,922B1 discloses a vagus nerve stimulation system for the treatment of epilepsy, which takes into account a measurement of the cardiac signal in order to optimize treatment, and more precisely in order to correct a stimulation intended to treat an epileptic seizure so as to prevent undesirable effects with respect to the heart rate. Furthermore, according to this document, only one stimulation in the afferent direction is appropriate for treating the epileptic seizure.

There are also numerous other documents on the stimulation of the vagus nerves, but none of them specifically deals with preventing the risk of sudden death when an epileptic seizure occurs. These include, in particular, US 2007/027486 A1 and US 2007/255320 A1.

Lastly, commercial solutions for stimulating the vagus nerve exist that aim to reduce the number of epileptic seizures in epilepsy patients, but these solutions are ineffectual in protecting patients against sudden death if a seizure occurs. An example of such a vagus-nerve neurostimulation system is sold by Cyberonics and is indicated for incapacitating or pharmacoresistant epilepsy.

SUMMARY OF THE INVENTION

The present invention aims to enable, on the one hand, the detection at the vagus nerve or preferably at both vagus nerves, if necessary in combination with one or more other physiological signals, of the occurrence of an abnormal and intense paroxysmal activity, likely to cause death (this activity probably being linked to an epileptic seizure, but the subject of the invention not being in itself to detect the occurrence of epileptic seizures) and, on the other hand, by acting on the vagus nerve or preferably both vagus nerves, substantially to reduce this risk of hyperactivity and death.

According to the invention according to a first aspect, a system is thus proposed intended to limit the risks of sudden death in the event of an epileptic seizure, characterized in that it comprises:
  a detection and control unit;
  at least one detection probe connected to the detection and control unit and intended to be applied to at least one of the two vagus nerves of a patient,
  means provided in the detection and control unit for detecting a phenomenon of mass discharge of action potentials in at least one vagus nerve using the detection probe or detection probes,
  at least one stimulation probe for stimulating a vagus nerve, and
  means provided in the detection and control unit that are capable, in response to the detection of a mass discharge, of applying predefined asymmetric stimulation signals to the stimulation probe(s) capable of causing a depolarization and/or hyperpolarization of the vagus nerve(s) and of blocking the conduction of the action potentials at least in the efferent direction.

The above system advantageously but optionally comprises the following additional characteristics, taken individually or in any combination that a person skilled in the art will deem technically compatible:
  the detection probe(s) and the stimulation probe(s) constitute the same probes;
  the mass discharge detection means are configured to determine an overall electrical energy density in at least one vagus nerve;
  the mass discharge detection means comprise a means of comparing an electrical energy in a set frequency band with a threshold;
  the electrical energy is determined by squaring and low-pass filtering a signal that has undergone low-pass filtering within said frequency band;
  which comprises two probes for stimulating the left and right vagus nerves;
  of which the stimulation signals are periodic and deterministic;

the asymmetry of the stimulation signals is chosen so as to achieve a depolarization of the nerve fibers of the vagus nerve(s);

the asymmetry of the stimulation signals is chosen so as to achieve a hyperpolarization of the nerve fibers of the vagus nerve(s);

the asymmetric periodic signals have a frequency of between around 15 and 300 kHz;

the stimulation signals comprise a succession of generally rectangular positive and negative current pulses, the amplitudes of the positive and negative pulses being different;

the current pulses of greater amplitude are shorter in duration than the current pulses of smaller amplitude;

the amplitudes and durations are chosen so that the balance of the electrical charges applied to the electrodes and taken from the electrodes is basically neutral;

the duration (TS) of the stimulation pulses is preset and lasts between around 0.5 and around 2 s;

the system comprises a means for determining the heart rate, and in which the pulses are applied until a heart rate above the threshold is resumed;

the detection and control unit also comprises an input for at least one signal chosen from a cardiac signal, a respiratory signal, an oxymetry signal and an electromyography signal;

the detection and control unit comprises an input for an electromyography signal, this signal being derived from the signal provided by the detection probe(s);

the system comprises detection probes configured to be positioned on both vagus nerves, and the mass discharge detection means are configured to operate on signals coming from both detection probes.

According to a second aspect of the invention, a method implemented in a system as described above is proposed for selectively generating electrical control signals of at least one probe of a vagus nerve of a patient with a view to containing the risks of sudden death in the event of an epileptic seizure, characterized in that it comprises the following steps:

detecting an electrical phenomenon supplied by at least one detection probe and representative of a mass discharge of action potentials in the vagus nerve;

in response to this detection, generating preset asymmetrical stimulation electrical signals intended to be applied to at least one stimulation probe and having the characteristics appropriate to cause on their application a depolarization and/or a hyperpolarization of the vagus nerve(s) and to block the conduction of the action potentials at least in the efferent direction.

Advantageously, the method also comprises a step of comparing a heart rate signal with a threshold, the generation of stimulation signals being performed in the event of detecting at the same time a mass discharge and the fact that the heart rate signal reveals a heart rate falling below a threshold.

In a similarly advantageous way, the method also comprises, after the step of generating stimulation signals, a step of comparing a heart rate signal with a threshold, and a new step of generating stimulation signals if the heart rate signal reveals a heart rate falling below a threshold.

Furthermore, the preferred but optional characteristics of the system apply equally to the above method.

BRIEF DESCRIPTION OF THE DRAWINGS

Further features, aims and advantages of the present invention will emerge more clearly from the following detailed description of a preferred embodiment thereof, given by way of non-limiting example with reference to the accompanying drawings, in which.

DETAILED DESCRIPTION OF A PREFERRED EMBODIMENT a) General Principle

The object of the system according to the invention is to prevent risks of death connected with epileptic seizures (basically by the phenomenon of "SUDEP"), on the one hand thanks to a certain characterization of an electrophysiological signal collected at the vagus nerve, preferably at both vagus nerves, and on the other thanks to a certain electrical stimulation, in the efferent direction, applied to the vagus nerve(s).

The characterization is performed by detecting a mass discharge in the efferent direction of the vagus nerve, as will be described later, using a probe placed around one of the two vagus nerves or preferably two probes placed around the left and right vagus nerves.

Possibly, this characterization can be combined with one or more other physiological signals of the patient, and in particular a cardiac signal and/or a respiratory signal and/or an oxymetry signal and/or an electromyographic signal.

The action of reducing the risk of sudden death is performed according to the invention by electrical stimulation on one of the vagus nerves or preferably on both vagus nerves, in conditions appropriate to neutralize the signals conveyed in the nerves. This neutralization can be achieved either by applying to the nerve(s) a depolarization, so as to cause an instantaneous inhibition due to the refractory period, or by applying to the nerve(s) a hyperpolarization, having a blocking effect due to the inhibition of excitability, for a controlled period of time.

In order to determine the optimum conditions of a depolarization or a hyperpolarization, it is particularly helpful to refer to the document "Conduction block in myelinated axons induced by high-frequency (kHz) non-symmetric biphasic stimulation," Z. Zhao et al., Frontiers in Computational Neuroscience, July 2015, Volume 9, Article 86, which suggests the possibility of using non-symmetric alternating electric wave forms, with a preponderance of their positive component or their negative component, respectively, to achieve a blocking of the conduction of action potentials in the different nerve fibers.

More particularly, a non-symmetric biphase electrical action can be used, in a first approach, with an alternating signal having longer positive pulses than the negative pulses, in order to create a hyperpolarization, and in a second approach, with an alternating signal having shorter positive pulses than the negative pulses, in order to create a depolarization.

Figure 4:
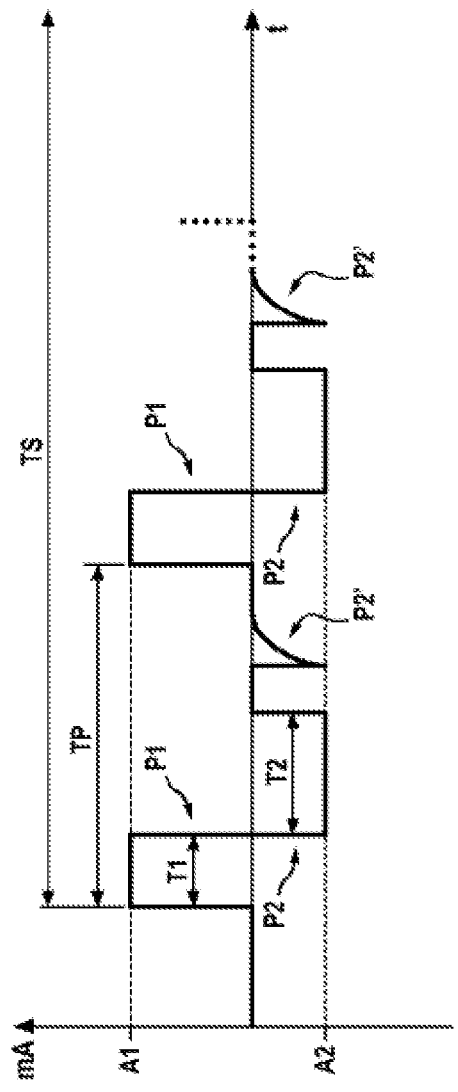

There now follows, with reference to FIG. 4, a concrete example of signals intended to cause a hyperpolarization of the vagus nerve.

Furthermore, it is possible to combine such stimulating electrical signal characteristics with the use of spatial selectivity probes. In particular, it is now known, thanks to specific structures of probe electrodes, to apply a stimulation in a preferential manner onto certain sections of the vagus nerve, in order to achieve this spatial selectivity. The depolarization or hyperpolarization can thus be applied in a preferred way onto certain nerve fibers, causing less disturbance to other fibers of which the conduction of action potentials has not necessarily been blocked. This spatial selectivity also allows the amplitude of the current required to block conduction to be reduced.

It is also possible to use the time dimension by performing depolarizations and/or hyperpolarizations according to different timings in different regions of the vagus nerve(s).

b) Detailed Implementation

Figure 1:
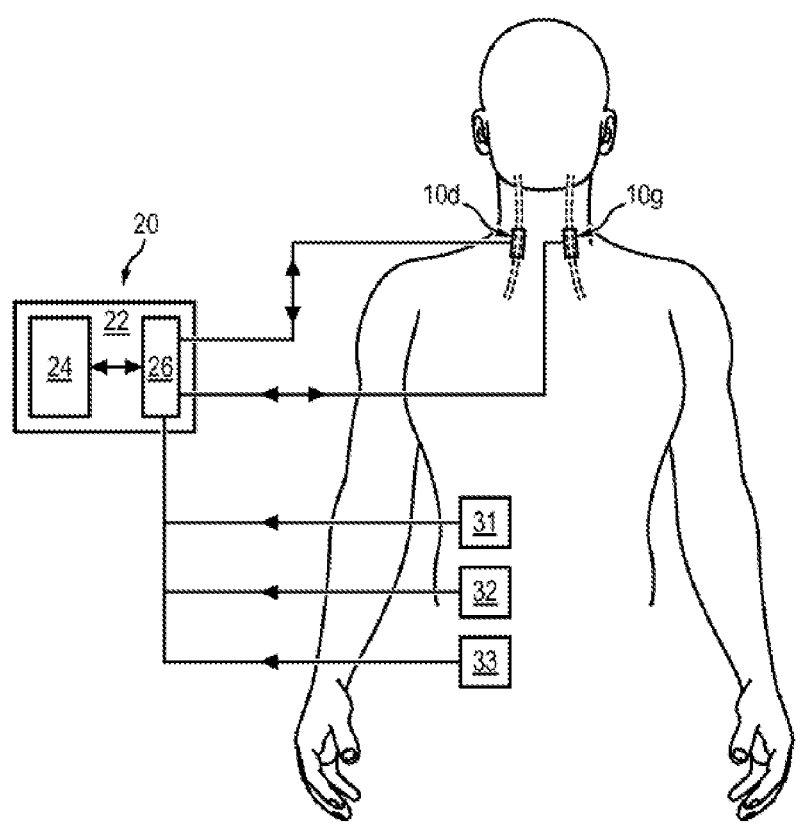
FIG. 1 is a schematic representation of a system according to the invention.
Figure 2:
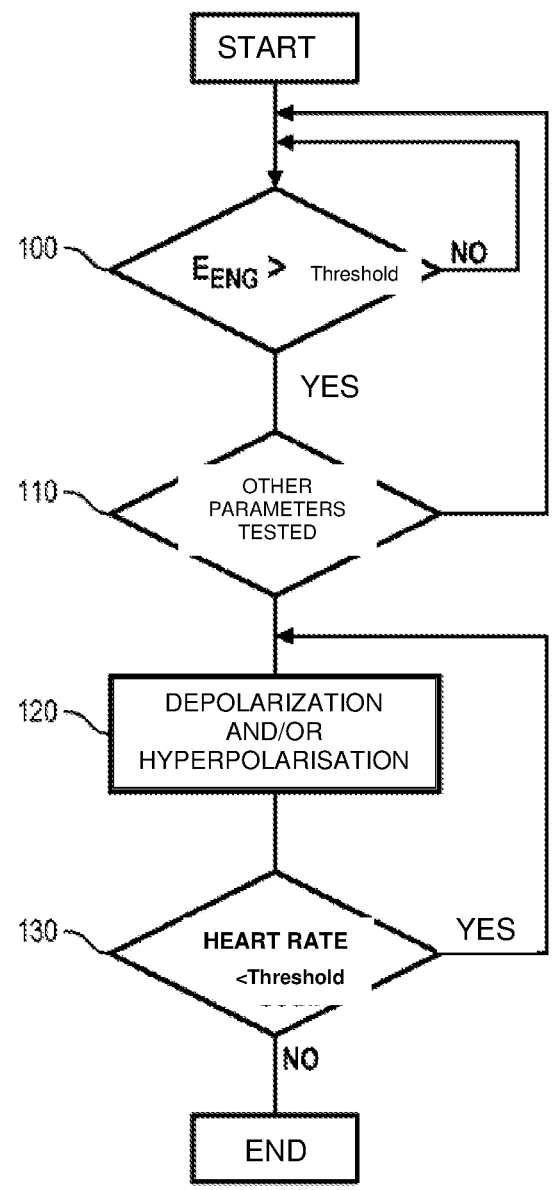
FIG. 2 shows a process implemented by the system according to the invention.

There now follows a description, with reference to FIGS. 1 and 2, of a more detailed implementation of the invention.

FIG. 1 shows the left and right vagus nerves of a patient, LVN and RVN respectively.

On each vagus nerve, a detection and neurostimulation probe has been implanted, 10g and 10d respectively. Each probe preferably comprises an electrode matrix specifically to create an electrical stimulation with spatial and/or temporal selectivity. Advantageously, the combination of electrodes, or possibly only one pair of this combination, is used also during periods of no treatment in order to detect mass discharge. This can be performed for one vagus nerve or both vagus nerves. In a particular embodiment, the invention can be implemented on only one of the two vagus nerves. In particular, as the right vagus nerve is basically responsible for the effects on heart rate (sinus node), a detection and a stimulation of depolarization and/or hyperpolarization can be envisaged on this nerve only. However, detection and stimulation can also be performed on the left vagus nerve, which is chiefly associated with the modulation of the atrioventricular node.

Both probes are connected by multi-stranded conductors to a unit 20, preferably of the portable or implantable type, comprising in a box 22 a central processing unit 24 and input/output circuits 26 through which the signals are applied to the probes 10g, 10d, and collected from said probes. A battery, not shown, powers the circuits of the unit 20.

The system also comprises a heart rate sensor 31 such as a pulse sensor or a cardiac probe, and if necessary a respiratory sensor 32 and/or an oxymetry sensor 33.

The heart rate sensor is used at least to determine, as will be seen later, whether a neutralization of the action potentials results in keeping the heart rate above a threshold, i.e. whether the risk of cardiac arrest has been eliminated.

It can also be used as an additional detector of an epileptic seizure likely to lead to sudden death, in combination with the detection of a mass discharge in at least one of the two vagus nerves. This additional detection can for example involve determining whether the heart rate exceeds the top and bottom preset thresholds, these excesses creating risk situations for the patient. It can also involve detecting the presence of atrioventricular blocks, which can be caused by a mass activation of a vagus nerve.

The respiratory sensor and/or oxymetry sensor make it possible to determine whether the respiratory function of the patient is being normally fulfilled. If a sensor is provided, the detection of a respiratory failure (reduction or absence of respiration muscle movements, or drop in the rate of oxygen in the blood) is combined with the detection of a mass discharge using at least one of the probes 10g, 10d to identify an epileptic seizure with risk of sudden death.

According to another improvement, the unit 20 can comprise means to analyze the electromyography signals so as to detect an abnormal muscle activity, due for example to the generalized tonicoclonic seizure often present before an SUDEP event. These signals can often be obtained directly by using the electrodes present in the detection probe(s) on the vagus nerve (capture of an ENG+EMG composite signal) or even between the stimulation box and one of the peripheral electrodes on the detection probe(s).

Preferably, the electromyographic analysis is performed in connection with step 110 of FIG. 2, and the stimulation is performed only when a muscle activity above a threshold is detected at the same time as the mass discharge phenomenon or prior to this phenomenon.

With reference now to FIG. 2, a preferred and simplified example of a process implemented using the system of FIG. 1 will now be described.

At step 100, the unit 20, which periodically collects the signals coming from at least one of the probes 10g and 10d, performs a calculation of the overall energy of the action potentials in the respective vagus nerve. Advantageously, this calculation is performed digitally, the signals forming the object of an analog/digital conversion in the circuit 26. Advantageously, it implements a band-pass filtering, for example on a band of between around 300 Hz and 3 kHz, and a time adjustment and integration, in a known way in the field of signal processing.

So as long as this energy does not exceed a given threshold, the test is periodically repeated by a closed loop command, for example with a period of 0.5 to 10 seconds.

When the unit detects that this energy is above a threshold, the other physiological parameters are then tested at step 110, although this step is optional. In particular, unit 20 can detect a heart rate window output, an atrioventricular block, a drop in respiratory activity below a threshold or even a muscle activity above a threshold, as explained above.

As long as these parameters remain within the normal ranges, the process is redirected upstream of step 100 and the global energy of the action potentials is again monitored.

If step 110, when it is envisaged, confirms a cardiac or respiratory anomaly, a depolarization and/or hyperpolarization cycle of the two vagus nerves using probes 10g, 10d is performed at step 120 in order to neutralize the action potentials at least in the efferent direction in the vagus nerves, as explained above.

Following this cycle, which may involve applying short bursts of depolarization and/or hyperpolarization signals, alternating and asymmetric as described above, unit 20 uses the signals of sensor 31 to determine at step 130 whether the heart rate is dropping below a certain threshold, for example in the order to 20 to 30 bpm depending on the patient. If it is, this means that the risk of death is always high and a new depolarization or hyperpolarization cycle is implemented, and so on. If it is not, the risk of sudden death can be eliminated with a certain reliability and the process is ended and a new monitoring process can be undertaken according to the timing defined in unit 20.

Figure 3:
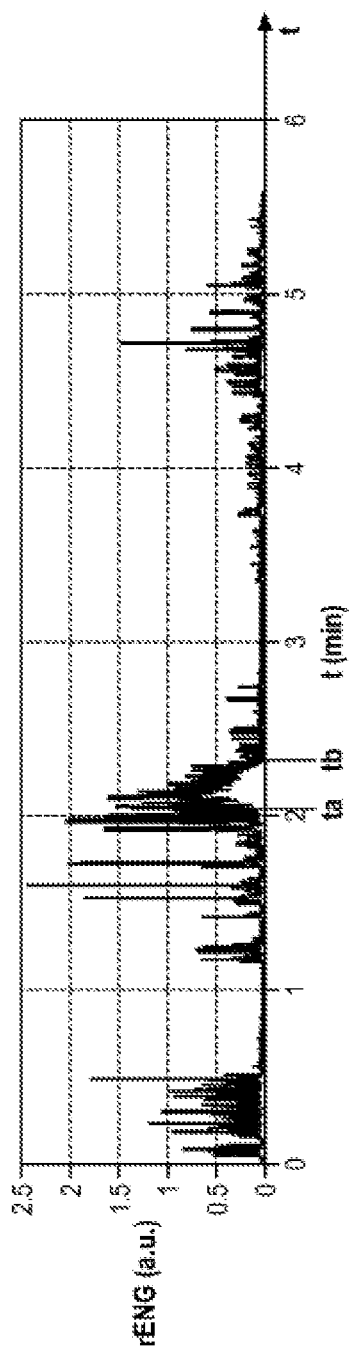
FIG. 3 gives an example of signals collected on a vagus nerve and showing a mass discharge phenomenon, and FIG. 4 gives an example of the appearance of stimulation signals applied to a vagus nerve stimulation probe.

FIG. 3 shows, by way of illustration, the signal resulting from processing by a band-pass filtering by filter 24a (FIG. 1), then a quadratic (squared) function by squaring unit 24b (FIG. 1) then a low-pass filtering by filter 24c (FIG. 1), of a signal acquired from a detection probe on a vagus nerve. This resulting signal incorporates elements of the electroneurogram and electromyogram, which can however be separated by filtration and additional processing of the signal.

FIG. 3 shows, between the time points ta and tb, a mass discharge phenomenon. It will be understood that, by the above-described processing, it is possible to detect a mass discharge. It is when this resulting signal exceeds a given threshold that a risk of sudden death during an epileptic seizure is identified.

FIG. 4 shows an example of stimulation signals applied to a vagus nerve probe according to the invention, with a view to achieving a hyperpolarization of the nerve in the efferent direction.

These signals comprise a succession of positive pulses of current P1 and negative pulses of current P2 of different durations, pulse P2 being followed by a pulse P2' of passive discharge, in a known way. In the case in question, the positive pulses of current have a greater amplitude, but a shorter duration, than the negative pulses. Advantageously, these amplitudes and these durations are chosen so that the balance of electrical charges applied to the vagus nerve and taken from the vagus nerve is neutral, so as to prevent the stimulation from electrically charging this region of the body.

Preferably, the duration mismatch between the positive pulses P1 and negative pulses P2 is between around 1 and 4 μs, depending on the frequency of the signal.

This frequency is advantageously between 15 and 300 kHz, and more preferably near 20 kHz or above 100 kHz in order to have the desired effect by minimizing the energy delivered.

Thus, for a frequency of 20 kHz, i.e. a total pulse duration of 50 μs (period TP in FIG. 4), it is possible to envisage for example a positive pulse P1 of a duration of 15 μs, a negative pulse of a duration of 18 μm, the remaining 17 μm being taken up by the passive discharge pulse and by a waiting time before the next positive pulse.

Depending on the nature and type of the probe, the electrical intensity of the stimulation signal can vary, but typically an intensity amplitude in the order of 3 to 5 mA is used. In order to obtain (at least approximately) the above-mentioned electrical neutrality, the amplitude of each positive pulse in the above-described digital example is 18-15 times greater than the amplitude of each negative pulse.

Moreover, the sequence of pulses P1, P2, P2' is repeated a certain number of times for a total duration (TS in FIG. 4) in the order of a few seconds, or even continuously until the mass discharge ceases or until a heart rate above the threshold is resumed.

In the above example, the stimulation performs a hyperpolarization of a vagus nerve in the efferent direction. By implementing negative pulses of current of greater amplitude than the positive pulses of current (more preferably of shorter durations), as a variation it is possible to achieve a depolarization of the vagus nerves in the efferent direction.

Clearly, numerous variations and modifications of the invention can be introduced. In particular:

- the mass discharge likely to indicate a physiopathological activity connected to an epileptic seizure likely to engender a sudden death phenomenon can be detected in one vagus nerve or in both vagus nerves identically or differently;
- the electrical action aimed at neutralizing the action potentials can be applied to both vagus nerves identically or differently;
- the probe(s) used for detecting a mass discharge can be the same probes as those used for the neutralization of the action potentials, or different probes;

The invention claimed is:

1. A system for reducing a risk of sudden death of a patient from an epileptic seizure, comprising:

a detection and control unit;
   at least one detection probe connected to the detection and control unit and adapted to be applied to at least one of two vagus nerves of the patient;
   at least one action potential blocking probe for applying electrical signals to the at least one vagus nerve;
   a detector provided in the detection and control unit for detecting global electrical energy density of action potentials in the at least one vagus nerve using the at least one detection probe, wherein the detector comprises a comparator for comparing said detected global electrical energy density of action potentials with a predetermined threshold indicating a massive discharge of action potentials in said at least one vagus nerve; and
   a signal generator provided in the detection and control unit and connected to said at least one action potential blocking probe and adapted to, in response to the comparator determining the detected global electrical energy density of action potentials to be higher than the predetermined threshold, apply depolarizing or hyperpolarizing asymmetric biphasic signals to said at least one action potential blocking probe to block a conduction of the action potentials at least in an efferent direction.

2. The system according to claim 1, wherein the at least one detection probe and the at least one action potential blocking probe constitute the same probes.

3. The system according to claim 1, wherein the detector further comprises a filter, the global electrical energy density of action potentials being detected in a frequency band determined by said filter.

4. The system according to claim 3, wherein the detector further comprises a circuit for squaring and low-pass filtering an output signal from said filter.

5. The system according to claim 1, which comprises two probes connected to the signal generator for applying electrical signals to both left and right vagus nerves.

6. The system according to claim 1, wherein said depolarizing or hyperpolarizing asymmetric biphasic signals applied to the at least one vagus nerve are periodic.

7. The system according to claim 6, wherein said depolarizing or hyperpolarizing asymmetric biphasic signals applied to the at least one vagus nerve have a frequency of between 15 and 300 kHz.

8. The system according to claim 7, wherein said depolarizing or hyperpolarizing asymmetric biphasic signals applied to the at least one vagus nerve comprise a succession of generally rectangular positive and negative current pulses, the amplitudes of the positive and negative current pulses being different.

9. The system according to claim 8, wherein the current pulses of greater amplitude are shorter in duration than the current pulses of smaller amplitude.

10. The system according to claim 9, wherein the amplitudes and durations of the current pulses are such that a balance of electrical charges applied to corresponding electrodes and taken from the corresponding electrodes is neutral.

11. The system according to claim 8, wherein a duration (TS) of the current pulses is between 0.5 and 2 s.

12. The system according to claim 8, further comprising a heart rate sensor, wherein the depolarizing or hyperpolarizing asymmetric biphasic signals are applied to the at least one vagus nerve until a heart rate above the threshold is resumed.

13. The system according to claim 1, wherein the detection and control unit also comprises an input for at least one signal chosen from a cardiac signal, a respiratory signal, an oxymetry signal and an electromyography signal.

14. The system according to claim 13, wherein the detection and control unit comprises an input for an electromyography signal, this signal being derived from the signal provided by the detection probe(s).

15. The system according to claim 1, comprising detection probes configured to be positioned on both vagus nerves and wherein the detector is configured to operate on signals obtained from both detection probes.

16. A method for reducing a risk of sudden death of a patient from an epileptic seizure, comprising the following steps:
providing at least one detection probe applied to at least one of two vagus nerves of the patient;
providing at least one action potential blocking probe for applying electrical signals to the at least one vagus nerve;
detecting a global electrical energy density of action potentials in the at least one vagus nerve using the at least one detection probe;
comparing said detected global electrical energy density of action potentials with a predetermined threshold indicating a massive discharge of action potentials in said at least one vagus nerve;
in response to a determination by the comparing that the detected global electrical energy density of action potentials is higher than said predetermined threshold, applying depolarizing or hyperpolarizing asymmetric biphasic signals to said at least one action potential blocking probe to block a conduction of the action potentials at least in an efferent direction of the corresponding at least one vagus nerve.

17. The method according to claim 16, further comprising, after the signal application step:
sensing a heart signal;
determining a heart rate from said heart signal;
comparing said heart rate signal with a threshold; and
applying another one or more of said depolarizing or hyperpolarizing asymmetric biphasic signals when the heart rate falls below the threshold.

18. The method according to 19, wherein said depolarizing or hyperpolarizing asymmetric biphasic signals applied to the at least one vagus nerve are periodic.

19. The method according to claim 18, wherein the depolarizing or hyperpolarizing asymmetric biphasic signals have a frequency of between 15 and 300 kHz.

20. The method according to claim 19, wherein a duration (TS) of the current pulses is between 0.5 and 2 s.

21. The method according to claim 16, wherein the depolarizing or hyperpolarizing asymmetric biphasic signals comprise a succession of generally rectangular positive and negative current pulses, the amplitudes of the positive and negative current pulses being different.

22. The method according to claim 21, wherein the current pulses of greater amplitude are shorter in duration than the current pulses of smaller amplitude.

23. The method according to claim 22, wherein the amplitudes and durations of the current pulses are such that a balance of electrical charges applied to corresponding electrodes and taken from the corresponding electrodes is neutral.

* * * * *